United States Patent [19]

Brange et al.

[11] Patent Number: 4,472,385
[45] Date of Patent: Sep. 18, 1984

[54] STABILIZED INSULIN PREPARATIONS AND METHOD FOR THEIR PRODUCTION

[75] Inventors: Jens J. V. Brange, Klampenborg; Svend Havelund, Hvidovre, both of Denmark

[73] Assignee: Novo Industri A/S, Denmark

[21] Appl. No.: 356,343

[22] Filed: Mar. 9, 1982

[30] Foreign Application Priority Data

Mar. 10, 1981 [GB] United Kingdom ............... 8107423
Sep. 18, 1981 [GB] United Kingdom ............... 814143

[51] Int. Cl.$^3$ ............................................. A61K 37/26
[52] U.S. Cl. .................................................. 424/178
[58] Field of Search ................. 260/112.7; 424/178, 424/153, 154

[56] References Cited

U.S. PATENT DOCUMENTS 2,474,729  6/1949  Durel et al. ................. 424/178
4,196,196  4/1980  Tiholiz ......................... 424/178

Primary Examiner—Frederick E. Waddell
Attorney, Agent, or Firm—Fidelman, Wolffe & Waldron

[57] ABSTRACT

Novel pharmaceutical preparations of dissolved insulin having improved physical stability particularly adapted for use in continuous insulin delivery equipment prepared by incorporating therein a calcium or magnesium salt so as to provide a solution containing essentially ionized calcium or magnesium in insulin stabilizing concentrations.

The magnesium or calcium ions concentrations are with the range of about $0.4 \times 10^{-3}$ to $10^{-2}$ molar.

7 Claims, No Drawings

STABILIZED INSULIN PREPARATIONS AND METHOD FOR THEIR PRODUCTION

The present invention relates to novel stabilized insulin preparations which are specifically adapted for use in equipment for continuous insulin delivery, and to a process for producing such stabilized insulin preparations.

INTRODUCTION

In recent years, steadily increasing efforts have been devoted to development of portable or implantable systems for continuous infusion of insulin. The main aim of such efforts is to put at the disposal of the diabetic patient a regime of insulin administration closer to diurnal variations in the patient's physiological insulin requirements than is possible by conventional insulin medication.

Essential to a device for continuous insulin delivery are such elements as an insulin reservoir, a pumping system and a suitable catheter for delivering the insulin to a chosen site, one usually located subcutaneously or intravenously or in the peritoneal space. The pumping system may be automatically activated and may also be provided with a voluntary control for delivering insulin at times of specific needs.

If the insulin solution is supplied by a syringe, the syringe will also usually function as the insulin reservoir. Devices of the syringe type are generally carried extracorporeally. However, more sophisticated systems have been developed, in which the system is constructed for implantation, usually subcutaneously with an insulin reservoir adapted for percutaneous refilling.

Efforts by workers in the art to develop systems for continuous infusion of insulin presupposes that the insulin solutions will remain stable during storage in the insulin reservoir, and, moreover, will not generate precipitates anywhere in the device; in the catheter, for example. In point of fact, the insulin art has discovered that the conventional insulin medication solutions are not sufficiently stable for continuous infusion purposes, forming precipitates in the catheter, for example. In addition, concentrated insulin solutions are desired for use in continuous infusion devices.

The propensity of insulin to precipitate out of commercially available conventional insulin medicament solutions, thereby obstructing both mechanical parts and delivery catheters, has proven to be a major impediment to development of, and safe clinical application of continuous infusion equipment. Furthermore, the obvious reasons for endeavoring to decrease ever the size of continuous delivery system creates a need for more concentrated insulin solutions than have been available heretofore, which may further aggravate the stability and precipitate problems.

Generally assumed by the art is that explanation of the precipitation phenomenon must be sought in the tendency of insulin to form insoluble fibrils, particularly when insulin solutions are maintained at elevated temperatures over extended periods of time. Evidently, any type of motion of or in the insulin solutions, including, for example, the turbulence induced by its passage through a narrow lumen or orifice, induces insulin fibrillation. Insulin solutions are subjected inescapably to several motion actions inside continuous delivery equipment. The general shortcomings of prior art insulin preparations in this respect are amply documented in the literature, for example, see the review article by W. D. Lougheed et al. (Diabetologia, Vol. 19 (1980) pp. 1–9).

To solve the precipitate problem proposals have been made to use acid insulin solutions or neutral insulin formulations containing a sugar, such as glucose (D. C. Schade et al.: Satelite-Symposium to 16th European Association for the Study of Diabetes Meeting, Greece, 22–23 Sept. 1980, p. 107) or containing a synthetic non-ionic surfactant (H. Thurow: German Patent Appln. No. P 29 52 119.5).

However, insulin is chemically unstable in acid solution, even at below body temperature levels and insulin may react, reversibly or irreversibly, with carbohydrates. Also, presence of a non-physiological surfactant could be regarded as undesirable in drugs for parenteral use. Such potential inconveniences are overcome according to the present invention.

OBJECTIVES OF THE INVENTION

A principal object of this invention is to provide novel insulin solutions from which the insulin is substantially less prone to precipitate under conditions prevailing in continuous insulin delivery equipment than has been the case with the heretofore conventional insulin preparations.

A further object of this invention is to provide a method for preparing stable insulin solutions.

RATIONALE OF THE INVENTION

The invention is based on the discovery that calcium and magnesium ions at certain concentrations can exert a stabilizing effect on insulin solutions. This is believed to be a surprising observation because calcium is known to form slightly soluble complexes with insulin, and to decrease the solubility of zinc insulin at neutral pH (J. E. Pitts et al.: Insulin, Chemistry, Structure and Function of Insulin and Related Hormones, p. 674 [Walther de Gruyter & Co., 1980]; S. O. Emdin et al.: Diabetologic 19 [1980] pp. 174–182).

BRIEF STATEMENT OF THE INVENTION

The present invention provides an insulin preparation suitable for use in continuous insulin infusion systems for being physically stabilized under conditions prevailing therein, which preparation comprises insulin in solution, a preserving agent, and calcium or magnesium ions at a concentration sufficient to impart stability to said solution, but insufficient to induce insulin precipitation under normal use conditions. Optionally present is a non-ionizing osmotic pressure regulating agent and/or a buffering agent which does not form complexes or slightly soluble compounds with calcium or magnesium ions.

A second aspect of the present invention provides a method for preparing an insulin solution suitable for use in continuous insulin infusion systems for being physically stabilized under conditions prevailing therein, which method is characterized by bringing the insulin into solution together with an essentially ionizable calcium or magnesium salt at a concentration sufficient to impart stability to said solution, but insufficient to induce insulin precipitation therein under normal conditions; further adding a preserving agent and, optionally, a non-ionizing osmotic pressure regulating agent and/or a buffering agent which does not form complexes or slightly soluble compounds with calcium or magnesium ions.

PREFERRED EMBODIMENTS OF THE INVENTION AND DETAILED DESCRIPTION THEREOF

Generally, the stability of insulin solutions (as measured by the test method described hereinafter) increases with increasing concentration of $Ca^{++}$ or $Mg^{++}$ up to a point. However, at increased concentration beyond this point almost instantaneous precipitation of insulin may occur. The concentration limit or danger point appears to be some function of insulin content and solution temperatures.

At ambient temperature the upper limit of the non-precipitating concentration for $Ca^{++}$ or $Mg^{++}$ decreases from about $10^{-2}$ molar to about $3 \times 10^{-3}$ molar over the concentration interval of insulin corresponding to from 5 to 50 international units (I.U.) per ml, and then decreases nominally to about $2 \times 10^3$ molar over the concentration interval corresponding to from 50 to 1000 I.U. per ml.

Restated, the preferred stable 5–1500 I.U. per ml insulin solutions of this invention contain therein $Ca^{++}$ or $Mg^{++}$ in concentrations in the range of $0.4 \times 10^{-3} - 10^2$ molar. To repeat, while concentrations of $10^2$ may not be feasible for higher insulin concentrations for reasons of precipitate formation, concentrations near to the precipitation point are preferred.

Thus, in preferred embodiments of the present invention, the molarity of calcium or magnesium ions in the preparation does not exceed the above described limits, including not being less than about $0.4 \times 10^{-3}$. Preferred are calcium or magnesium salts of inorganic acids, such as hydrochloric, sulphuric and nitric acid, the calcium salts being most preferred.

Preferably, the total molar concentration of other metal salts than those of calcium or magnesium, such as sodium salts, does not exceed 0.01, and the presence of calcium or magnesium precipitating or complexing anions, such as phosphate, gluconate, citrate or acetate, is avoided in the insulin solutions of this invention. Hence if isotonicity and buffering capacity in the insulin solution is desired, the former is preferably established by means of a non-electrolyte, such as glycerol, and the latter by means of a non-complexing buffer, such as TRIS.

Another preferred embodiment involves the use of zinc insulin, preferably porcine, bovine or human insulin, in which the zinc content does not exceed 1% by weight (calculated on the basis of dry insulin crystals).

The concentration of insulin in the solutions of this invention is in the range of from 5 to 1,500 I.U., preferably from 40 to 1,000 I.U. per ml.

The method of preparing the insulin solutions of the present invention comprises dissolving crystalline insulin, for example, a highly purified grade of insulin, such as "monocomponent" insulin (see British Pat. No. 1,285,023) in water in the presence of acid, for example, hydrochloric acid. An aqueous solution of the preserving agent, for example, phenol or an alkyl phenol, such as cresol, or methyl parahydroxybenzoate, prepared separately, may, if desired, also contain an osmotic pressure regulating agent such as glycerol, preferably in amounts calculated to render the final insulin solution isotonic. The preservative solution is then added to the acid insulin solution followed by addition of a base, for example, sodium hydroxide solution, to adjust pH to neutrality. Within the context of this invention, neutrality is to be understood as a pH value in the range or from about 7 to about 8. The insulin solutions of this invention are at a pH in the range of pH 7–8.

The calculated amounts of calcium or magnesium salt, as for instance, calcium chloride dihydrate, or magnesium chloride hexahydrate, and a buffering agent (if such is desired in the insulin solution) such as TRIS are added to insulin solution at this stage, followed by readjustment of pH. Alternatively, the calcium or magnesium salt may be dissolved in the acid insulin solution prior to neutralization thereof. The resulting insulin solution is finally filled up to the calculated volume with water, then sterilized by filtration and subsequently transferred to sterile vials.

STABILITY TEST

The insulin solutions so prepared are subjected to a stability test under forced conditions in the following manner:

Vials (of 12.5 ml capacity) containing the test sample (10 ml) and each provided with a rubber cap are placed vertically on a shaking platform (e.g., Type 01 T623TBSH02, HETO, Birkerod, Denmark) which is totally immersed in a water bath kept at $41° C. \pm 0.1° C$. The platform is subjected to horizontal rocking movements with a frequency and amplitude of 100 rpm and 50 mm, respectively.

The opalescence of the test samples is monitored at regular time intervals on a (Fisher DRT 1000) nephelometer provided with an adapter for vials. Fibrillation time is defined as the lapse of time until the test sample develops a turbidity of 10 nephelometric turbidity units (NTU).

Each test is conducted with test samples and control samples without added calcium or magnesium salt (4–5 vials of each) treated side by side. The stability factor is calculated as the ratio of the average fibrillation time of the test samples to that of the control samples.

EXAMPLES

For further understanding of practice of the present invention, the following Examples are provided.

In the Examples, aqueous solutions and water were sterilized, the former by filtration, and subsequent operations thereof were conducted under aseptic conditions.

EXAMPLE 1

500 I.U. insulin per ml in $2 \times 10^{-3}$ molar solution of calcium chloride Crystalline monocomponent porcine insulin (7.44 g) containing 0.4 percent of zinc and having a total activity of 200,000 I.U. was dissolved in water (250 ml) containing hydrochloric acid (6.5 ml of N), followed by the addition of an aqueous solution (100 ml) containing glycerol (6.4 g) and phenol (0.8 g). The pH of the solution was adjusted to 7.5 by means of sodium hydroxide solution, and the total volume made up to 400 ml with water. To an aliquot of this solution (100 ml) was added 29.4 mg calcium chloride dihydrate and the resulting solution was sterilized by filtration and subsequently transferred aseptically to vials (10 ml). Stability factor: $>25:1$

EXAMPLE 2

500 I.U. insulin per ml in $3 \times 10^{-3}$ and 0.02 molar solution of calcium chloride and TRIS, respectively Crystalline monocomponent porcine insulin (3.72 g) containing 0.4% zinc and having a total activity of 100,000 I.U. was dissolved in water (125 ml) containing hydrochloric acid (3.25 ml of N), followed by the addition of an aqueous solution (50 ml) containing glycerol (3.2 g) and phenol (0.4 g). The pH was adjusted to 7.5 by means of sodium hydroxide solution. TRIS (0.48 g) and calcium chloride (88 mg of dihydrate) were added. The pH was readjusted to 7.5 with hydrochloric acid and the volume made up to a total of 200 ml with water. The resulting solution was sterilized by filtration and subsequently transferred aseptically to vials (10 ml). Stability factor: 5:1

EXAMPLE 3

500 I.U. insulin per ml in $0.5 \times 10^{-3}$ molar solution of calcium chloride Crystalline monocomponent porcine insulin (5.58 g) containing 0.4 percent zinc and having a total activity of 150,000 I.U. was dissolved in water (150 ml) containing hydrochloric acid (4.9 ml of N) and calcium chloride (22 mg of dihydrate) followed by the addition of an aqueous solution (100 ml) containing glycerol (4.8 g) and phenol (0.6 g).

The pH of the solution was adjusted to 7.5 by means of sodium hydroxide solution and the total volume to 300 ml with water. The resulting solution was sterilized by filtration and subsequently transferred aseptically to vials (10 ml). Stability factor: 2.3:1

EXAMPLE 4

500 I.U. insulin per ml in $2 \times 10^{-3}$ molar solution of calcium chloride The procedure was analogous to that of example 3, except that 88 mg of calcium chloride dihydrate was added thus affording a solution containing 0.002M calcium chloride. Stability factor: >25:1

EXAMPLE 5

200 I.U. insulin per ml in $2 \times 10^{-3}$ molar solution of calcium chloride 300 ml of an insulin solution prepared according to example 4 was diluted with 450 ml of a neutral aqueous solution containing glycerol (7.2 g), phenol (0.9 g) and calcium chloride (132 mg of dihydrate). The resulting insulin solution containing 200 I.U./ml was sterilized by filtration and transferred aseptically to vials (10 ml).

Stability factor: 12:1

EXAMPLE 6

40 I.U. insulin per ml in $2 \times 10^{-3}$ molar solution of calcium chloride

Crystalline monocomponent porcine insulin containing 0.4 percent of zinc and having a total activity of 40,000 I.U. was dissolved in 120 ml water containing hydrochloric acid (1280 $\mu$l of N) followed by addition of an aqueous solution (730 ml) of phenol (2 g) and glycerol (16 g). An aqueous solution (40 ml) containing sodium hydroxide (2000 $\mu$l of N) was added, followed by addition of an aqueous solution (15 ml) containing calcium chloride (220 mg of dihydrate). Finally the pH was adjusted to 7.4 by means of sodium hydroxide solution, and the total volume to 1000 ml with water. The solution was sterilized by filtration and subsequently transferred aseptically to vials (10 ml).

Stability factor: 3:1

EXAMPLE 7

500 I.U. insulin per ml in $(2 \times 10^{-3})$ molar solution of magnesium chloride Crystalline monocomponent porcine insulin (3.72 g) containing 0.4% zinc and having a total activity of 100,000 I.U. was dissolved in water (125 ml) containing hydrochloric acid (3.25 ml of N), followed by the addition of an aqueous solution (50 ml) containing glycerol (3.2 g) and phenol (0.4 g). The pH was adjusted to 7.5 by means of sodium hydroxide solution. Magnesium chloride (81 mg of hexahydrate) was added, pH readjusted to 7.5 with sodium hydroxide and the volume made up to a total of 200 ml with water. The resulting solution was sterilized by filtration and subsequently transferred aseptically to vials (10 ml).

Stability factor: 6:1

EXAMPLE 8

100 I.U. insulin per ml in $(2 \times 10^{-3})$ molar solution of magnesium chloride Crystalline monocomponent porcine insulin (3.72 g) containing 0.4% zinc and having a total activity of 100,000 I.U. was dissolved in water (125 ml) containing hydrochloric acid (3.25 ml of N), followed by the addition of an aqueous solution (800 ml) containing glycerol (16 g) and phenol (2 g). The pH was adjusted to 7.5 by means of sodium hydroxide solution. Magnesium chloride (407 mg of hexahydrate) was added, pH readjusted to 7.5 and the volume made up to a total of 1000 ml with water. The resulting solution was sterilized by filtration and subsequently transferred aseptically to vials (10 ml). Stability factor: 4:1

EXAMPLE 9

100 I.U. human insulin per ml in $2 \times 10^{-3}$ molar solution of calcium chloride Crystalline semisynthetic human insulin, prepared by the method described in British Patent Application No. 2,069,502 A, (2.04 g) containing 0.4% zinc and having a total activity of 55.000 I.U. was dissolved in water (275 ml) containing hydrochloric acid (1.8 ml of N). To an aliquot of this solution (25 ml) was added calcium chloride dihydrate (14.7 mg) followed by the addition of an aqueous solution (20 ml) containing glycerol (0.8 g) and phenol (0.1 g). The pH of the solution was adjusted to 7.4 by means of sodium hydroxide solution and the total volume to 50 ml with water.

The resulting solution was sterilized by filtration and subsequently transferred aseptically to vials (10 ml).

Stability factor: 7:1.

We claim:

1. An insulin preparation adapted to use in continuous insulin infusion systems consisting essentially of zinc insulin in solution, a preserving agent and, optionally, a non-ionizing osmotic pressure regulating agent and/or a buffering agent which does not form complex or slightly soluble compounds with calcium or magnesium ions, which preparation contains calcium or magnesium ions at a concentration within the range of about $0.4 \times 10^{-3}$ molar to about $10^{-2}$ molar but insufficient to induce precipitation therein under normal conditions, the calcium or magnesium imparting physical stability to said solution, the pH of said preparation being within the range of 7 to 8.

2. The insulin preparation according to claim 1, wherein the calcium or magnesium ions are furnished as salts of hydrochloric, sulfuric or nitric acid.

3. The insulin preparation according to claim 1, wherein the ion is calcium.

4. The insulin preparation according to claim 1, wherein the insulin concentration is in the range of from 5 to 1500 international insulin units per ml.

5. The insulin preparation according to claim 4 wherein the insulin is in the range of from 40–1000 international insulin units per ml.

6. A method of stabilizing zinc insulin for use in continuous insulin infusion systems comprising bringing insulin into solution together with an essentially ionizable calcium or magnesium salt to impart stability to the insulin solution, in concentration within the range of about $0.4 \times 10^{-3}$ to $10^{-2}$ molar but insufficient to induce insulin precipitation therein under normal conditions; further adding a preserving agent and, optionally, a non-ionizing osmotic pressure regulating agent and/or a buffering agent which does not form complex or slightly soluble compounds with calcium or magnesium ions.

7. The method of claim 6, wherein the insulin and preserving agent, the latter optionally in the presence of osmotic pressure regulating agent and/or buffering agent, are dissolved separately and then admixed before the calcium or magnesium salt is added.

* * * * *